US007547769B2

(12) United States Patent
Fraser

(10) Patent No.: US 7,547,769 B2
(45) Date of Patent: Jun. 16, 2009

(54) IMMUNOMODULATORY CONSTRUCTS AND THEIR USES

(75) Inventor: John David Fraser, Auckland (NZ)

(73) Assignee: Auckland Uniservices Limited, Auckland (NZ)

(*) Notice: Subject to any disclaimer, the term of this patent is extended or adjusted under 35 U.S.C. 154(b) by 171 days.

(21) Appl. No.: 10/516,813

(22) PCT Filed: Jun. 4, 2003

(86) PCT No.: PCT/NZ03/00111

§ 371 (c)(1),
(2), (4) Date: Jul. 5, 2005

(87) PCT Pub. No.: WO03/101173

PCT Pub. Date: Dec. 11, 2003

(65) Prior Publication Data

US 2006/0246067 A1    Nov. 2, 2006

(30) Foreign Application Priority Data

Jun. 4, 2002    (NZ) ..................................... 519371

(51) Int. Cl.
*C07K 14/00* (2006.01)
*C07K 17/00* (2006.01)
*C08H 1/00* (2006.01)
(52) U.S. Cl. ..................................... 530/403; 530/350
(58) Field of Classification Search ........................ None
See application file for complete search history.

(56) References Cited

U.S. PATENT DOCUMENTS

| 5,116,964 | A | 5/1992 | Capon et al. |
| 5,545,716 | A | 8/1996 | Johnson et al. |
| 5,698,679 | A | 12/1997 | Nemazee |
| 5,728,388 | A | 3/1998 | Terman |
| 5,858,363 | A | 1/1999 | Dohlsten et al. |
| 5,859,207 | A | 1/1999 | Johnson et al. |
| 5,968,514 | A | 10/1999 | Johnson et al. |
| 6,042,837 | A | 3/2000 | Kalland et al. |
| 6,095,315 | A | 8/2000 | Andersch et al. |
| 6,126,945 | A | 10/2000 | Terman et al. |
| 6,180,097 | B1 | 1/2001 | Terman |
| 6,197,299 | B1 | 3/2001 | Dohlsten et al. |
| 6,221,351 | B1 | 4/2001 | Terman |
| 6,251,385 | B1 | 6/2001 | Terman |
| 6,338,845 | B1 | 1/2002 | Terman |
| 6,340,461 | B1 | 1/2002 | Terman |
| 6,514,498 | B1 | 2/2003 | Antonsson et al. |
| 6,692,746 | B1 | 2/2004 | Terman et al. |
| 2003/0092894 | A1 | 5/2003 | Antonsson et al. |

FOREIGN PATENT DOCUMENTS

| EP | 0 766 566 | 4/2001 |
| WO | WO 93/14634 | 8/1993 |
| WO | WO 00/39159 | 7/2000 |
| WO | WO 02/11619 | 2/2002 |
| WO | 02/45739 | 6/2002 |

OTHER PUBLICATIONS

Parks et al., May 2002, J. General Virol. vol. 83: 1167-1172.*
Yan et al., "Characterization of Monoclonal Antibodies to the 26-kDa Glutathione S-transferase of Schistosoma japonicum", 1996, Hybridoma, vol. 15:429-33.
Hong-Gellar et al., "Therapeutic approaches to superantigen-based disease: a review", 2003, J. Mol. Rec., vol. 16:91-101.
Arcus et al. "Conservation and variation in superantigen structure and activity highlighted by the three-dimensional structures of two new superantigens from *streptococcus pyogenes*". Biology 299:157-168, 2000.
Proft et al. "The streptococcal superantigen SMEZ exhibits wide allelic variation, mosaic structure, and significant antigenic variation". J. Exp. Med. 191(10):1765-1776, May 2000.
Unnikrishnan et al. "The bacterial superantigen streptococcal mitogenic exotoxin Z is the major immunoactive agent of *streptococcus pyogenes*". The Journal of Immunology 169:2561-2569, 2002.
Li et al. "Three-dimensional structure of the complex between a T cell receptor β chain and the superantigen staphylococcal enterotoxin B". Immunity 9:807-816, Dec. 1998.
Fraser et al. "Superantigens—powerful modifiers of the immune system". Molecular Medicine 6:125-132, Mar. 2000.
Leder et al. "A Mutational analysis of the binding of staphylococcal enterotoxins B and C3 to the T cell receptor β chain and major histocompatibility complex class II". J. Exp. Med. 187(6):823-833, Mar. 1998.
Lukas Leder et al. "A mutational analysis of the binding of staphylococcal enterotoxins B and C3 to the T cell receptor beta chain and major histocompatibility complex class II". Journal of Experimental Medicine 187(6):823-833, Mar. 16, 1998.
Hongmin Li et al. "Three-dimensional structure of the complex between a T cell receptor beta chain and the superantigen staphylococcal exterotoxin B". Immunity 9(6):807-816, Dec. 1998.
John Fraser et al. "Superantigens: Powerful modifiers of the immune system". Molecular Medicine Today 6(3):125-132, Mar. 2000.
McCormick, John K. et al. "Development of Streptococcal Pyrogenic Exotoxin C Vaccine Toxoids that are Protective in the Rabbit Model of Toxic Shock Syndrome." *The Journal of Immunology* (2000), pp. 2306-2312.
Nestle et al., "Human Dermal Dendritic Cells Process and Present Soluble Protein Antigens", The Journal of Investigative Dermatology, vol. 110, No. 5, May 1998, pp. 762-766.

* cited by examiner

*Primary Examiner*—G. R Ewoldt
*Assistant Examiner*—Amy E Juedes
(74) *Attorney, Agent, or Firm*—Occhiuti Rohlicek & Tsao LLP

(57) ABSTRACT

The invention relates to immunomodulators. In particular the invention relates to specific immunomodulators based on the superantigen SMEZ-2 and more particularly based on mutants of the superantigen SMEZ-2, which are adapted to target antigen-presenting-cells for the purpose of enhancing or suppressing a host immune response.

19 Claims, 7 Drawing Sheets

Generation of SMEZ-2 TcR mutants

FIGURE 1

SMEZ mutant

Inhibition of tumour growth in mice with 1 μg M1-LCMV peptide

Figure 5 Enhancement of antibody responses to antigens coupled to SMEZ2-M1

Figure 5

Coupling of LCMV peptide to SAG increases its antigenicity for CTL

- LCMV peptide
- SPEC-LCMV
- W75L.K182Q.D42C SMEZ2-LCMV
- W75L.K182Q.D42C.Y18.A SMEZ2-LCMV
- W75L.K182Q.D42C.Y18.A SMEZ2 + LCMV uncoupled

Figure 6

SEQUENCE LISTING

```
<160> NUMBER OF SEQ ID NOS: 13

<210> SEQ ID NO 1
<211> LENGTH: 209
<212> TYPE: PRT
<213> ORGANISM: Streptococcus pyogenes

<400> SEQUENCE: 1

Leu Glu Val Asp Asn Asn Ser Leu Leu Arg Asn Ile Tyr Ser Thr Ile
1               5                   10                  15

Val Tyr Glu Tyr Ser Asp Ile Val Ile Asp Phe Lys Thr Ser His Asn
            20                  25                  30

Leu Val Thr Lys Lys Leu Asp Val Arg Asp Ala Arg Asp Phe Phe Ile
        35                  40                  45

Asn Ser Glu Met Asp Glu Tyr Ala Ala Asn Asp Phe Lys Thr Gly Asp
    50                  55                  60

Lys Ile Ala Val Phe Ser Val Pro Phe Asp Trp Asn Tyr Leu Ser Lys
65                  70                  75                  80

Gly Lys Val Thr Ala Tyr Thr Tyr Gly Gly Ile Thr Pro Tyr Gln Lys
                85                  90                  95

Thr Ser Ile Pro Lys Asn Ile Pro Val Asn Leu Trp Ile Asn Gly Lys
            100                 105                 110

Gln Ile Ser Val Pro Tyr Asn Glu Ile Ser Thr Asn Lys Thr Thr Val
        115                 120                 125

Thr Ala Gln Glu Ile Asp Leu Lys Val Arg Lys Phe Leu Ile Ala Gln
    130                 135                 140

His Gln Leu Tyr Ser Ser Gly Ser Ser Tyr Lys Ser Gly Arg Leu Val
145                 150                 155                 160

Phe His Thr Asn Asp Asn Ser Asp Lys Tyr Ser Phe Asp Leu Phe Tyr
                165                 170                 175

Val Gly Tyr Arg Asp Lys Glu Ser Ile Phe Lys Val Tyr Lys Asp Asn
            180                 185                 190

Lys Ser Phe Asn Ile Asp Lys Ile Gly His Leu Asp Ile Glu Ile Asp
        195                 200                 205

Ser

<210> SEQ ID NO 2
<211> LENGTH: 209
<212> TYPE: PRT
<213> ORGANISM: Streptococcus pyogenes

<400> SEQUENCE: 2

Leu Glu Val Asp Asn Asn Ser Leu Leu Arg Asn Ile Tyr Ser Thr Ile
```

```
                 1               5                  10                 15
Val Tyr Glu Tyr Ser Asp Ile Val Ile Asp Phe Lys Thr Ser His Cys
                20                  25                  30

Leu Val Thr Lys Lys Leu Asp Val Arg Asp Ala Arg Asp Phe Phe Ile
                35                  40                  45

Asn Ser Glu Met Asp Glu Tyr Ala Ala Asn Asp Phe Lys Thr Gly Asp
                50                  55                  60

Lys Ile Ala Val Phe Ser Val Pro Phe Asp Trp Asn Tyr Leu Ser Lys
 65                  70                  75                  80

Gly Lys Val Thr Ala Tyr Thr Tyr Gly Gly Ile Thr Pro Tyr Gln Lys
                85                  90                  95

Thr Ser Ile Pro Lys Asn Ile Pro Val Asn Leu Trp Ile Asn Gly Lys
                100                 105                 110

Gln Ile Ser Val Pro Tyr Asn Glu Ile Ser Thr Asn Lys Thr Thr Val
                115                 120                 125

Thr Ala Gln Glu Ile Asp Leu Lys Val Arg Lys Phe Leu Ile Ala Gln
                130                 135                 140

His Gln Leu Tyr Ser Ser Gly Ser Ser Tyr Lys Ser Gly Arg Leu Val
145                 150                 155                 160

Phe His Thr Asn Asp Asn Ser Asp Lys Tyr Ser Phe Asp Leu Leu Tyr
                165                 170                 175

Val Gly Tyr Arg Asp Gln Glu Ser Ile Phe Lys Val Tyr Lys Asp Asn
                180                 185                 190

Lys Ser Phe Asn Ile Asp Lys Ile Gly His Leu Asp Ile Glu Ile Asp
                195                 200                 205

Ser

<210> SEQ ID NO 3
<211> LENGTH: 209
<212> TYPE: PRT
<213> ORGANISM: Streptococcus pyogenes

<400> SEQUENCE: 3

Leu Glu Val Asp Asn Asn Ser Leu Leu Arg Asn Ile Tyr Ser Thr Ile
 1               5                  10                  15

Val Ala Glu Tyr Ser Asp Ile Val Ile Asp Phe Lys Thr Ser His Cys
                20                  25                  30

Leu Val Thr Lys Lys Leu Asp Val Arg Asp Ala Arg Asp Phe Phe Ile
                35                  40                  45

Asn Ser Glu Met Asp Glu Tyr Ala Ala Asn Asp Phe Lys Thr Gly Asp
                50                  55                  60

Lys Ile Ala Val Phe Ser Val Pro Phe Asp Trp Asn Tyr Leu Ser Lys
 65                  70                  75                  80

Gly Lys Val Thr Ala Tyr Thr Tyr Gly Gly Ile Thr Pro Tyr Gln Lys
                85                  90                  95

Thr Ser Ile Pro Lys Asn Ile Pro Val Asn Leu Trp Ile Asn Gly Lys
                100                 105                 110

Gln Ile Ser Val Pro Tyr Asn Glu Ile Ser Thr Asn Lys Thr Thr Val
                115                 120                 125

Thr Ala Gln Glu Ile Asp Leu Lys Val Arg Lys Phe Leu Ile Ala Gln
                130                 135                 140

His Gln Leu Tyr Ser Ser Gly Ser Ser Tyr Lys Ser Gly Arg Leu Val
145                 150                 155                 160

Phe His Thr Asn Asp Asn Ser Asp Lys Tyr Ser Phe Asp Leu Leu Tyr
```

-continued

```
                165                 170                 175
Val Gly Tyr Arg Asp Gln Glu Ser Ile Phe Lys Val Tyr Lys Asp Asn
            180                 185                 190

Lys Ser Phe Asn Ile Asp Lys Ile Gly His Leu Asp Ile Glu Ile Asp
        195                 200                 205

Ser

<210> SEQ ID NO 4
<211> LENGTH: 27
<212> TYPE: DNA
<213> ORGANISM: Artificial sequence
<220> FEATURE:
<223> OTHER INFORMATION: Primer

<400> SEQUENCE: 4
cgattgtagc tgaatattca gatatag                                          27

<210> SEQ ID NO 5
<211> LENGTH: 27
<212> TYPE: DNA
<213> ORGANISM: Artificial sequence
<220> FEATURE:
<223> OTHER INFORMATION: Primer

<400> SEQUENCE: 5
gaatattcag ctacaatcgt actatag                                          27

<210> SEQ ID NO 6
<211> LENGTH: 24
<212> TYPE: DNA
<213> ORGANISM: Artificial Sequence
<220> FEATURE:
<223> OTHER INFORMATION: Primer
<220> FEATURE:
<223> OTHER INFORMATION: Primer

<400> SEQUENCE: 6
gatgttagat gtgctagaga tttc                                             24

<210> SEQ ID NO 7
<211> LENGTH: 26
<212> TYPE: DNA
<213> ORGANISM: Artificial sequence
<220> FEATURE:
<223> OTHER INFORMATION: Primer

<400> SEQUENCE: 7
ctctagcaca tctaacatca agtttc                                           26

<210> SEQ ID NO 8
<211> LENGTH: 23
<212> TYPE: DNA
<213> ORGANISM: Artificial sequence
<220> FEATURE:
<223> OTHER INFORMATION: Primer

<400> SEQUENCE: 8
ccatttgatt tgaactattt atc                                              23

<210> SEQ ID NO 9
<211> LENGTH: 23
<212> TYPE: DNA
<213> ORGANISM: Artificial sequence
<220> FEATURE:
<223> OTHER INFORMATION: Primer
```

```
<400> SEQUENCE: 9
gataaatagt tcaaatcaaa tgg                                              23

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
gatatagaga tcaagaaagt atc                                              23

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
gatactttct tgatctctat atc                                              23

<210> SEQ ID NO 12
<211> LENGTH: 18
<212> TYPE: DNA
<213> ORGANISM: Artificial sequence
<220> FEATURE:
<223> OTHER INFORMATION: Primer

<400> SEQUENCE: 12
accatcctcc aaaatcgg                                                    18

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
tcagaggttt tcaccgtc                                                    18
```

IMMUNOMODULATORY CONSTRUCTS AND THEIR USES

TECHNICAL FIELD

This invention relates to immunomodulators and their use. In particular, it relates to specific immunomodulators based on the superantigen SMEZ-2 and more particularly based on mutants of the superantigen SMEZ-2, which are adapted to target antigen-presenting-cells for the purpose of enhancing or suppressing a host immune response. The invention also relates to methods of enhancing antigenicity of compounds using said constructs, as well as to novel SMEZ-2 mutants.

BACKGROUND ART

Professional antigen-presenting-cells (APC) are essential to initiate a primary immune response in a non-immune, naive animal. The most important APC is the Dendritic Cell (DC), which is found as an interdigitating cell at all regions of the body, at an interface with the environment (i.e. skin and mucosal surfaces such as the lung, airways, nasal passage etc). Antigens presented by DCs are profoundly immunogenic. One important phenotypic marker of the DC is a very high level of surface MHC class II expression. Activated DCs migrate to secondary lymph nodes to "prime" both CD4 and CD8 T cells which proceed as antigen activated effector cells, to proliferate, produce cytokines and regulate the humoral response of B-lymphocytes. Thus, antigen presentation by DC appears to be the obligate first step in any adaptive immune response. Other APCs such as macrophages and B-cells appear to be important in later, secondary responses and by themselves are not effective in the initial priming of a response. Thus the DC is generally regarded as the most important cell to target for enhancement of immune responses.

The targeting of antigens to DC can however be problematic. For example, many peptides by themselves are poorly antigenic and immunogenic because they are not efficiently delivered to APC in vivo. They are equally not taken up by APC very efficiently and do not elicit the second signals required for efficient antigen presentation.

Superantigens are a family of semi-conserved bacterial proteins that target the immune system by binding simultaneously to the T cell Receptor (TcR) via the Vβ domain on T lymphocytes and MHC class II molecules expressed on APC including dendritic cells.

Superantigens (SAgs) are the most potent immune mitogens known and activate large numbers of T cells at femto-attomolar concentrations ($10^{-15}$-$10^{-18}$M). They cause significant toxicity due to the massive systemic cytokine release by T cells. There are currently 19 members of the staphylococcal and streptococcal superantigen family.

Terman (WO 98/26747)[1] discloses therapeutic compositions employing superantigens. It is suggested that superantigens, in conjunction with one or more additional immunotherapeutic antigens, may be used to either induce a therapeutic immune response directed against a target or to inhibit a disease-causing immune response. Terman further describes the formation of immunotherapeutic antigen-superantigen polymers. Such polymers include those where the superantigen component is coupled to a peptide antigen by a secondary amine linkage. However, there is no teaching or suggestion by Terman that the superantigen component be one from which the TcR binding function has been wholly or partly ablated. Indeed, there is no recognition that a TcR binding is not essential to activation of APCs and to stimulation of an immune response against the antigenic component of the polymer.

Thus, wild-type SAgs, or modified SAgs which retain the ability to bind to TcR, are of little use because they themselves elicit massive, indiscriminate T cell responses by binding to the TcR. This TcR cross-linking appears to be the major cause of their toxicity[2].

There exists a need therefore for improved immunomodulators which exploit the unique features of DC targeting and activation of SAgs to deliver and enhance the T cell recognition of antigens such as peptides that are normally non-immunogenic or have low immunogenicity, yet are efficacious and have low toxicity.

It is an object of the present invention to overcome or ameliorate at least some of the disadvantages of the prior art, or to provide a useful alternative.

SUMMARY OF THE INVENTION

According to a first aspect of this invention there is provided an immunomodulator which comprises an antigen-presenting-cell (APC) targeting molecule coupled to an immunomodulatory antigen, wherein said APC targeting molecule mimics the superantigen SMEZ-2 but does not include a fully functional T-cell receptor binding site.

According to a second aspect there is provided an immunomodulator which comprises an antigen-presenting cell (APC) targeting molecule coupled to an immunomodulatory antigen, wherein said APC targeting molecule is a molecule which is structurally a SMEZ-2 superantigen but for a disrupted T-cell receptor binding site such that the molecule has little or no ability to activate T-cells.

Preferably the coupling between the SMEZ-2 antigen-presenting-cell (APC) targeting molecule and the immunomodulatory antigen is reversible.

Preferably the immunomodulatory antigen is a protein or a peptide.

The immunomodulatory antigen may be entirely non-immunogenic when not coupled to the antigen-presenting cell (APC) targeting molecule but the immunomodulators of the present invention may also incorporate antigens which are immunogenic, in order to improve their efficacy. Thus the present invention is equally applicable for example to new vaccines as it is to those which are already known and used but which can be improved by means of the immunomodulators of the present invention.

In another aspect, the invention provides an immunomodulator which comprises SMEZ-2 having one or more mutations at positions 18, 42, 75 and 182 of the amino acid sequence thereof coupled to an immunomodulatory antigen. Preferably, the mutations are chosen from the group consisting of:

Y18A;

W75L;

K182Q; and

D42C.

In another aspect, the invention provides an immunomodulator which comprises SMEZ-2 having the mutations Y18A, W75L, K182Q, and D42C, coupled to an immunomodulatory antigen.

In another aspect, the invention provides an immunomodulator which comprises SMEZ-2 having the mutations W75L, K182Q, and D42C, coupled to an immunomodulatory antigen.

In yet a further aspect the invention provides an immunomodulator which comprises a defective TcR binding SMEZ-2 coupled to ovalbumin or tetanus toxoid (TT).

According to a further aspect there is provided a pharmaceutical composition comprising an immunomodulator according to the present invention and one or more pharmaceutically acceptable carriers, adjuvants, excipients and/or solvents.

According to yet a further aspect there is provided a vaccine comprising an immunomodulator according to the present invention.

According to a fifth aspect there is provided a method of therapeutic or prophylactic treatment of a disorder which requires the induction or stimulation of the immune system, comprising the administration to a subject requiring such treatment of an immunomodulator or of a pharmaceutical composition according to the present invention.

Preferably the disorder is selected from the group consisting of bacterial, viral, fungal or parasitic infection, autoimmunity, allergy and/or pre-neoplastic or neoplastic transformation.

According to another aspect there is provided the use of an immunomodulator according to the invention for the preparation of a medicament for the therapeutic or prophylactic treatment of a disorder which requires the induction or stimulation of the immune system.

The preferred disorder is selected from the group consisting of bacterial, viral, fungal or parasitic infection, autoimmunity, allergy and/or preneoplastic or neoplastic transformation.

According to a further aspect there is provided a method of preparing an immunomodulator comprising the steps of:
  a introducing a modification and/or a deletion into the T-cell binding site of an antigen-presenting cell (APC) targeting molecule which is structurally a SMEZ-2 superantigen, and
  b coupling thereto an immunomodulatory antigen.

It will be understood however that more than one antigen-presenting cell (APC) targeting molecule may be employed and that a combination of immunomodulators may be used in any treatment.

In another aspect, the invention provides SMEZ-2 having one or more mutations at positions 18, 42, 75 and 182 of the amino acid sequence of SEQ ID NO: 1. Preferably, the mutations are chosen from the group consisting of:
  Y18A;
  W75L;
  K182Q; and
  D42C.

In another aspect, the invention provides a superantigen SMEZ-2 having the mutations Y18A, W75L, K182Q, and D42C.

In another aspect, the invention provides a superantigen SMEZ-2 having the mutations W75L, K182Q, and D42C.

In a related aspect, the invention provides a nucleic acid encoding SMEZ-2 having one or more mutations at positions 18, 42, 75 and 182 of the amino acid sequence of SEQ ID NO:1.

BRIEF DESCRIPTION OF THE FIGURES

FIG. 1 Mitogenicity of SMEZ-2 (M1) mutants. The M1 mutant containing point mutations at Y18A.W75L.K182.D42C no longer stimulates human T cells. Human peripheral T cells were stimulated with varying concentrations of mutant SMEZ-2 proteins and their proliferation measured after 4 days incubation.

FIG. 5 Effects on antibody responses to an antigen coupled to M1. Ovalbumin (egg albumin) is a protein that produces poor antibody responses in mice Balb/c mice. Ovalbumin chemically conjugated to M1, generated 16-fold higher titres of an anti ovalbumin IgG1 antibody compared to mice immunised with ovalbumin and M1 unconjugated.

FIG. 6 Effect of SAG-LCMV peptide coupling on antigenicity for CTL.

DESCRIPTION OF THE PREFERRED EMBODIMENT

The present invention is based at least in part on an observation that a molecule which mimics a superantigen but which lacks a fully functional TcR binding site can, when coupled to an immunomodulatory antigen, bind and activate APCs to a degree not previously known or suspected.

This result was disclosed by the inventors in WO 02/45739. The present application is directed to the use in immunomodulators of specific molecules which mimic the superantigen SMEZ-2. The immunomodulators of this invention retain the enhanced delivery capacity and APC activating potential of the TcR ablated superantigens and the specificity of a coupled antigen as is discussed in WO 02/45739. However, the inventors have demonstrated particularly strong efficacy and potency above that expected using immunomodulators based on SMEZ-2 (particularly those SMEZ-2 mutants described herein after). It is noted that these constructs display better than expected MHC response.

The immunomodulators of the invention may also be referred to herein as "immunomodulatory constructs" or simply "constructs".

As APC-targeting molecules, a variety of defective TcR binding superantigens or mimics thereof have been selectively tested. These specifically include mutants of SMEZ-2, as detailed herein after. SMEZ-2 is an allelic variant of SMEZ.

Figure 1:
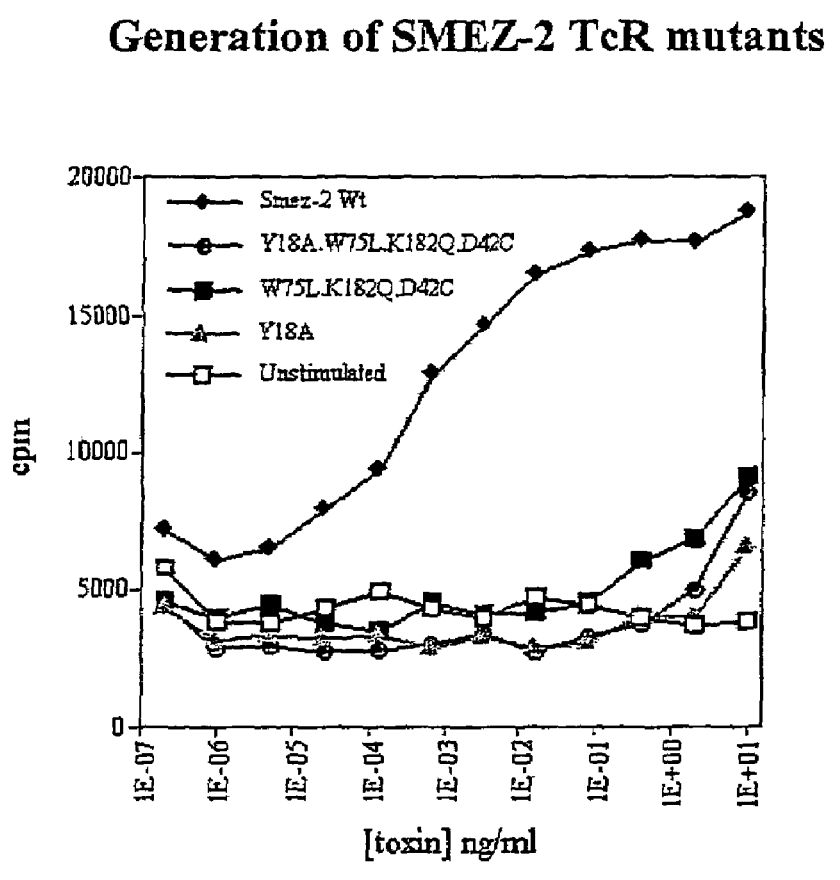

Targeted mutagenesis of the TcR binding site was completed to generate a mutant with a $>10^5$ fold decrease in T cell mitogenicity. FIG. 1 illustrates a $>10^5$ fold decrease in T cell mitogenicity for specific SMEZ-2 mutants which include up to four specific point mutations on one SMEZ-2 molecule.

Defective TcR binding SMEZ-2 for use in SMEZ-2-based constructs of the invention are preferably selected from SMEZ-2 having one or more mutations at positions 18, 42, 75, 182 of the amino acid sequence for SMEZ-2 as detailed herein (SEQ ID NO:1). More preferably the defective TcR binding SMEZ-2 mutant includes one or more of the following mutations: Y18A, W75L, K182Q and D42C. Particularly preferred SMEZ-2 mutants of use in the invention are described in Table 1 below.

TABLE 1

| Mutant |
|---|
| SMEZ-2 W75L |
| SMEZ-2 D42C |
| SMEZ-2 W75L.D42C.K182Q (M1) |
| SMEZ-2 Y18A |
| SMEZ-2 W75L.D42C.K182Q.Y18A. (M2) |

Figure 2:
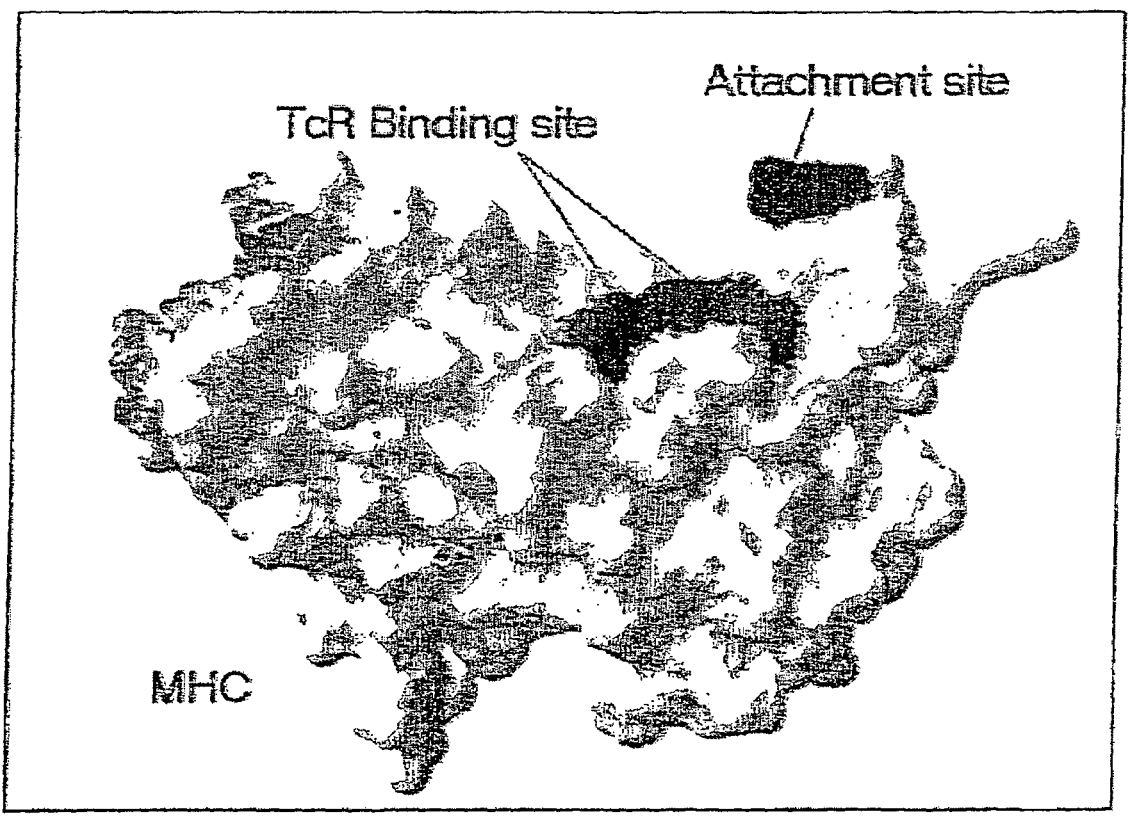
FIG. 2 A SMEZ-2 mutant. Three dimensional structure of the M1 mutant indicating the position of mutated TcR residues (blue) and attachment site (red). Location of the MHC class II binding site is also shown.
Figure 3:
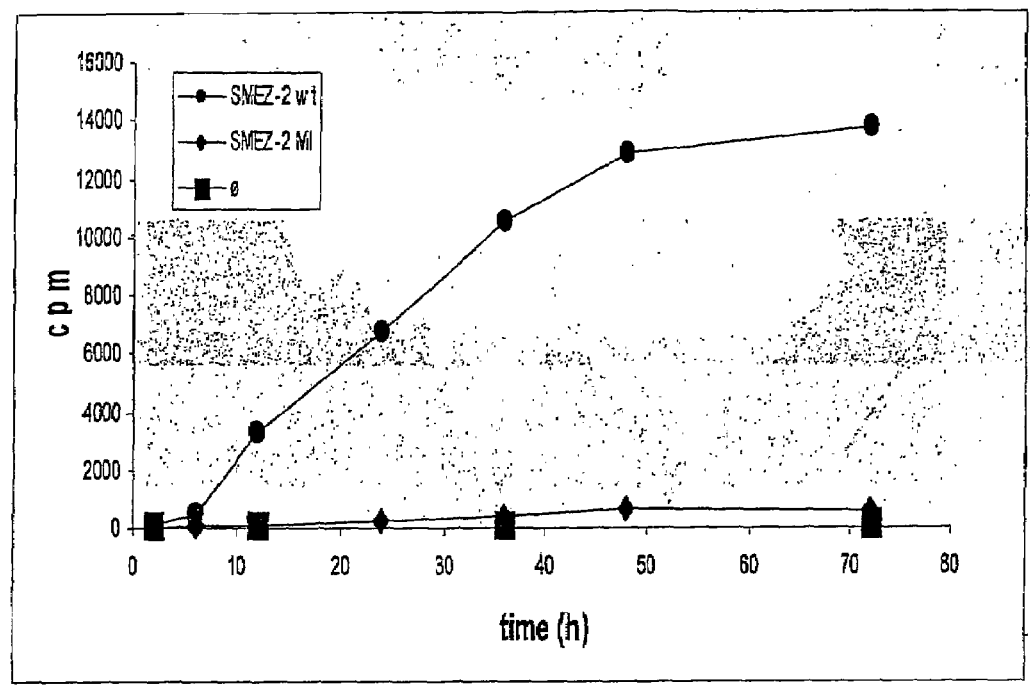
FIG. 3 The M1 mutant produces substantially no interleukin2 when added to human peripheral lymphocytes in culture and a reduced amount of tumour necrosis factor alpha (TNFa). Both cytokines are responsible for the toxic effects to the wild-type superantigen. This demonstrates the advantages of using at least the M1 mutation to produce constructs.
Figure 3:
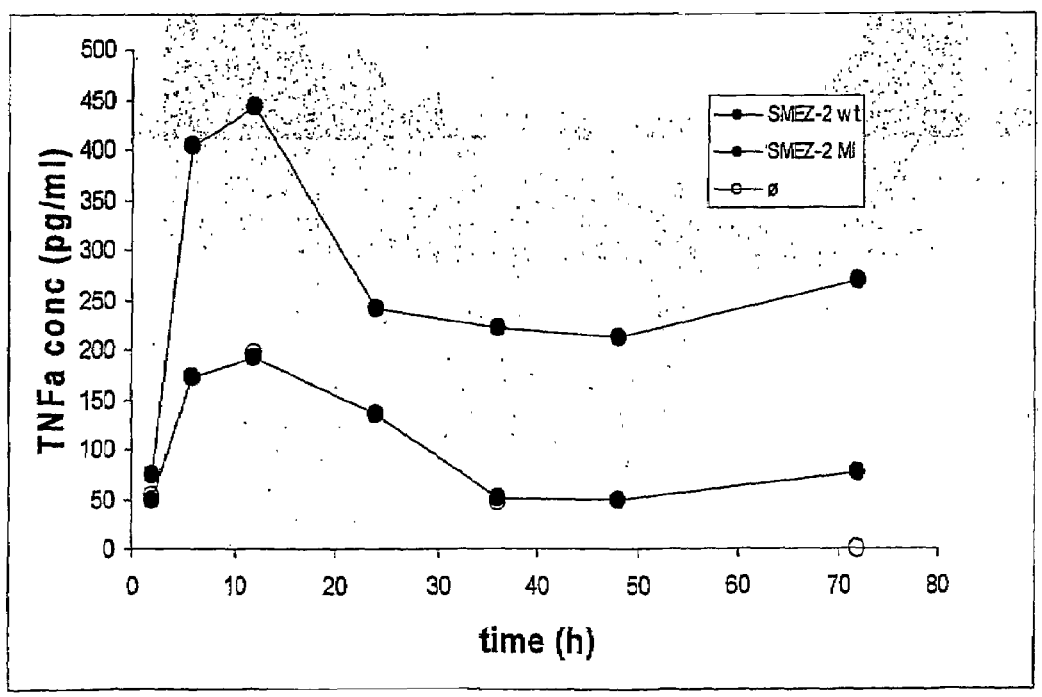

FIG. 2 illustrates a 3-D structural picture of an M1 developed from the crystal structure of the molecule. The structural picture of the M1 mutant shows the TcR binding site mutants (blue) and the active MHC attachment site (red). It will be appreciated by those skilled in the art that the position of the MHC binding site is some distance away from the TcR binding site. Further residues which are involved in TcR binding and recognition do not appear to be involved with MHC binding. This means that it is possible to disrupt by mutation the TcR binding properties of SMEZ-2 substantially without reducing MHC binding affinity.

Mutations may be created in wild-type SMEZ, particularly SMEZ-2, by any means known in the art. A preferred method involves the use of overlap PCR. As it will be appreciated by skilled persons, this technique generally involves the use of two complimentary overlapping synthetic primers which hybridise to specific sequences in the wild-type gene template contained in a bacterial plasmid in which the specific mutation is to be introduced. The primers contain a mutation within the overlap region. Extension of the primers allows for the synthesis of a new nucleic acid strand containing the specific mutation. The mutated nucleic acid plasmid is then introduced into bacteria to produce the recombinant mutant protein. Specific examples of techniques which may be used to arrive at the SMEZ-2 mutants of use in the present invention are provided herein after under the heading "Examples".

Persons skilled in the art will appreciate various antigens that may be coupled to an APC-targeting molecule of the invention. Such antigens may be referred to herein as "immunomodulatory antigens". These may include native or recombinant polypeptides, proteins, Whole and/or disabled viruses, nucleic acids, and also carbohydrate antigens. It will be appreciated that nucleic acids and polypeptides of use in the invention may be synthetically produced. Skilled persons will readily appreciate means of obtaining or making appropriate antigens for use in the invention.

The immunomodulatory constructs of the invention can be prepared for a range of antigens as above mentioned including those which may or may not necessarily be immunogenic. This has the advantage of providing or improving immunogenicity of an antigen or reducing the quantity of antigen required to induce an immune response.

For example, a protein known to generate protective immunity for a particular pathogen can be made more immunogenic by first conjugating the protein to a defective TcR binding SMEZ-2 molecule. The peptide protein would be broken down internally by the APC to present multiple restricted peptide epitopes to the host immune system. Antiviral immunity might be enhanced by adding on molecules that selectively target the virus to APCs such as dendritic cells.

Antigens can be designed to be either stimulatory (i.e. generate agonist responses) or immunosuppressive (i.e. generate antagonist responses) to induce tolerance depending on the primary sequence of the peptide. This is useful in either promoting immunity for vaccination against pathogens such as viruses, bacteria and other micro-organisms, or for generating specific anti-tumour immunity using tumour specific peptides.

Antagonist responses induce T cell tolerance to antigen and might be useful to suppressing unwanted autoimmune reaction to self-antigens eg. proteins and/or nucleic acids, in the case of diseases such as multiple sclerosis, diabetes or rheumatoid arthritis.

Many autoimmune diseases have their basis in an autoreactive T cell response to self antigens. Diseases such as rheumatoid arthritis, multiple sclerosis and diabetes mellitus are such examples.

The antigens ovalbumin (FIG. 5) and peptides of tetanus toxoid have been used to demonstrate the efficacy of SEMZ-2 based immunomodulators of the invention. Persons skilled in the art to which the invention relates will readily appreciate how immunomodulators containing these antigens may be used and the effects that attaching an antigen to the superantigen has on specific immune responses. However, by way of example an immunomodulator based on tetanus toxoid or peptides thereof may find use in tetanus vaccination protocols to enhance the response to tetanus antigens and to reduce the amount of antigen required.

By way of further example, immunomodulators of the invention may include as an immunomodulatory antigen an LCMV (lymphocyte choriomeningitis virus) peptide, preferably which has the amino acid sequence CKAVYNFATM. The inventor's studies, as detailed herein after, indicate constructs containing this peptide may find use in helping to inhibit tumour growth, and thus in the treatment or amelioration of cancers.

The coupling of the APC targeting molecule, more specifically a TcR-disrupted SMEZ-2 molecule, to an antigen can be accomplished by using any number of techniques standard in the art. It should be appreciated that the term "coupling" is intended to include any means by which the APC targeting molecule may be associated with one or more immunomodulatory antigens, and includes fusion, chemical linkage and the like. For example, the constructs may be produced recombinantly in the form of fusion proteins with the antigen formed as a genetic extension of either the C-terminus or N-terminus of the superantigen. Special consideration is preferably made to ensure the antigen does not interfere with MHC class II binding. Alternatively, the antigen and the APC targeting molecule may be coupled in accordance with techniques described herein after under the heading "Examples" or as described in WO02/45739.

By way of a general method, the APC targeting molecule may be coupled to an antigen using succinimidyl-S-acetylthiopropionate (SATP, Pierce Chemicals). In a first step the antigen undergoes a thiolation process using SATP. The antigen is first dissolved in $NaPO_4$ whilst SATP in dissolved in dimethylsulfoxide (DMSO). The SATP solution is added to the protein at a molar ratio of 1:1 and incubate at room temperature for 2 hours. Unbound SATP is removed by passing through VIVASPIN concentrator (5 kDa size exclusion), at about 10000 rpm for about 5 minutes. $NaPO_4$, is added and repeated 5 times [3]. Alternatively the antigen is passed through a column of sephadex G25 desalting column. Immediately after removal of free SATP the sulphydryl group of antigen-SATP is deprotected by a deacetylation process. This may be achieved by using a deacetylation solution including NaPO$_4$, EDTA, and Hydroxylamine-HCl. The defective TcR binding SMEZ-2 is then added to the solution in a 1:10 molar ration of SMEZ-2 to protein-SATP. A coupling buffer may also be added as will be readily known in the art. The defective TcR binding SMEZ-2 and protein-SATP are then incubated at room temperature for about 2 hours.

If the antigen has a naturally occurring cysteine residue, coupling to SMEZ-2 may be achieved directly without the need to introduce a reactive sulphydryl group. In this case, coupling would follow the established procedure outlined above.

If the antigen does not have a naturally occurring cysteine, a number of standard procedures may be used to introduce a reactive sulphydryl group. By way of example, a cysteine residue can be introduced genetically into the recombinant peptide and the polypeptide expressed from a heterologous expression system (prokaryotic or eukaryotic). It will be readily appreciated by those skilled in the art that the site of introducing the reactive sulphydryl group is preferably exposed on the surface of the molecule. Skilled persons will readily be able to identify such residues on the basis of actually or putative 3D protein structure.

By way of further example, recombinant SMEZ-2: antigen constructs may be constructed by extending the C-terminus of SMEZ-2 by creating a flexible linker of 5 to 10 glycine residues in a genetic construct according to standard methodology. Furthermore a nucleic acid construct may be provided which includes a multi-cloning site to allow the addition of selected antigen or peptide gene sequences. The entire construct may then be expressed to create a recombinant fusion construct protein.

By way of another example, an alternative coupling process may include the use of Streptavidin coupled to SMEZ-2. Streptavidin binds 4 molecules of biotin tightly. This creates a SMEZ-2 streptavidin fusion construct that allows the multivalent attachment of biotinylated proteins and peptides. In accordance with standard methodology, an antigen is biotinylated then added to the SMEZ-2 streptavidin fusion construct to form the final conjugate. Such coupling may be completed in accordance with techniques readily known in the art.

In a preferred embodiment of the invention the coupling between the APC targeting molecule and the antigen is reversible. What is particularly preferred is that the APC targeting molecule is capable of releasing the immunomodulatory antigen so that it is correctly presented by the APC. It will be recognised by persons of skill in the art to which the invention relates that the release of the antigen from the construct may be achieved by intracellular or intralysosomal enzymatic cleavage. This process may be assisted by introducing the appropriate proteolytic site into the coupling region of the construct. The release may also be achieved by chemical means, which includes oxidation/reduction reactions involving disulphides and free sulphydryl groups. This process may also be assisted by introducing into the coupling region certain amino acid residues, eg. cysteine. Persons of general skill in the art will readily appreciate techniques by which such cleavage or release sites may be incorporated into the constructs. However, by way of example, site directed mutagenesis, recombinant cloning and/or expression, chemical synthesis of peptides or nucleic acids coding therefore, which include appropriate sites.

Coupling need not be limited to individual peptides. Because immune responses to peptides are tightly restricted by the MHC polymorphisms of the host, it may be appropriate in some circumstances, to immunise with sets of peptides to generate broad spectrum immunomodulatory agents. Multiple peptides representing various components of a larger antigen such as a virus, bacteria or other protein antigen may be coupled by procedures described above or modified versions therefor which would be clear to those skilled in the art, to provide a mixed antigen:SMEZ-based construct antigen response to increase the diversity of the construct. Moreover, the ratio of peptides could be easily controlled to fine tune the immune response to a more desired outcome.

In addition, larger structures such as viruses can be "coated" with a TcR defective superantigens, specifically SMEZ-based, more particularly SMEZ-2-based superantigens, by first treating the virus with a chemical that introduces a reactive sulphydryl group.

The purification of SMEZ-2: antigen constructs may be performed by any appropriate means. Those of general skill in the art to which the invention relates will readily appreciate appropriate techniques having regard to the nature of the construct and the method by which it may have been generated. However, by way of example, constructs of the invention may be purified by HPLC and/or by size exclusion chromatography on HPLC using Superose12 column or any other suitable chromatography media that allows separation of proteins on the basis of size as may be well known in the art.

In addition to the individual immunomodulatory constructs, the invention also provides pharmaceutical compositions containing them along with one or more pharmaceutically acceptable carriers, adjuvants, excipients and/or solvents.

The phrase "pharmaceutically acceptable carriers, adjuvants, excipients and/or solvents", is intended to include substances that are useful in preparing a formulation, may be co-administered with the immunomodulatory constructs of the invention while allowing them to perform their intended function, and are generally safe, non-toxic and are neither biologically or otherwise undesirable. Acceptable pharmaceutical carriers, adjuvants, excipients and/or solvents will include those suitable for veterinarian use as well as human use. Examples of acceptable pharmaceutical diluents, carriers, and/or excipients include solutions, solvents, dispersions, media, delay agents, emulsions, fillers and the like.

Those skilled in the art will readily appreciate that a variety of acceptable pharmaceutical carriers, adjuvants, excipients and/or solvents may be employed in preparing a composition of the invention. As will be appreciated the choice of acceptable pharmaceutical carriers, adjuvants, excipients and/or solvents, may be dictated to some extent by the intended dosage form of the composition and the mode of administration of the composition.

Examples of suitable carriers, excipients, and solvents include alum and TitreMax.

As will be appreciated by persons of ordinary skill in the art to which the invention relates, the choice of adjuvant may differ depending on a number of variables. By way of example, the chemical nature of the adjuvant and its mode of action in a particular subject, the level of adjuvancy required, the observed side effects of a particular adjuvant, the nature of the antigen used, the tolerance of a particular subject to an adjuvant, which species of animal the subject belongs to, and the age and/or general health of a subject. Examples of suitable adjuvants may include: oil-based adjuvants (for example, Freunds complete or incomplete, mineral oil, emulsified peanut oil (adjuvant 65), paraffin and vegetable oils), liposomes, mineral compounds, aluminum hydroxide, aluminum phosphate, calcium phosphate, endotoxins, cholesterol, fatty acids, aliphatic amines, monophosphoryl lipid A, immunostimulating complexes (ISCOMs) (for example ISCOMs with Quil-A), and Syntex adjuvant formulations (SAFs) containing the threonyl derivative or muramyl dipeptide.

In addition to carriers, adjuvants, excipients and/or solvents, a composition of the invention may be formulated with additional constituents, or in such a manner, so as to help protect its integrity, for example. For example, the composition may further comprise constituents which provide protection against proteolytic degradation.

Skilled persons may appreciate additional ingredients which may be included in compositions of the invention.

Compositions of the invention may be produced by a number of techniques standard in the art by mixing the individual ingredients with one or more solvents, carriers adjuvants and/or excipients.

It is envisaged that a variety of different diseases and illnesses may be treated and/or prevented with the use of constructs or compositions of the invention. For example, the invention may have applications in the treatment of viral and bacterial infections or diseases.

As used herein, the term "treatment", or variations thereof, is to be considered in its broadest context. The term does not necessarily imply that an animal is treated until total recovery. Accordingly, "treatment" includes amelioration of the symptoms or severity of a particular condition or preventing or otherwise reducing the risk of developing a particular condition.

By way of example, the constructs may find use in relation to many viral infections where it may be desirable to stimulate long-lasting protection against infection such as with HIV, Hepatitis B, Hepatitis C and Corona (including sudden acute respiratory syndrome (SARS)) viral infections as examples. These viruses represent infections which are common and/or virulent amongst the population and which alternative treatments are desired. An HIV based construct could be formed from various HIV non-polymorphic surfaces or core antigens, for example.

The invention may also find use in relation to bacterial infections where it may be desirable to stimulate long-lasting protection against infection include Tuberculosis, *Pseudomonas* antigens, *Haemophilis influenza, Naiseria Meningococcus*. Again, these merely represent a selection of bacterial infections where the current invention may have applications and there is considerable medical relevance currently attached. Antigens or peptides could be prepared on the basis of cell surface and secreted antigens or peptides from bacteria.

Furthermore, the constructs of the invention may have application in anti-tumour treatments and for the treatment of autoimmune diseases. Coupled antigens or peptides can be prepared from tumours such as melanomas and solid tumours in order to generate a specific anti-tumour immune response; for example, LCMV may be used as antigen in a construct of the invention (as detailed herein after). Peptides or proteins coupled to TcR-defective SMEZ-2 can be used to suppress the immune response in patients with auto-immune diseases such as multiple sclerosis.

It will be appreciated that a composition and/or construct of the invention may be administered as any dosage form known in the art. Preferably injectable liquids are used. However, dosage forms such as orally administrable liquids, tablets, capsules, pills, granules, suspensions and emulsions, and sprays (atomiser or aerosol) may be used.

Compositions and/or constructs of the invention are preferably administered by intravenous or intramuscular injection. However, skilled persons will readily recognise alternative administration routes having regard to the condition to be treated and the dosage form used, for example.

As will be appreciated, the dose administered, the period of administration, and the general administration regime may differ between subjects depending on such variables as their tolerance to the constructs, weight, metabolism, the mode of administration chosen, the severity of symptoms, and the age and/or general health of a subject.

In further embodiments of the present invention, and applying the principles described herein, the following can also be accomplished:

MHC class I and class II restricted peptides may be combined to provide improved helper CD4 and cytolytic CD8 effector cells.

Immunodominant peptides from more than one viral antigen may be combined to promote selective anti-viral immunity.

Peptides from regions of viral antigens that do not normally predominate in the protective immune response but represent regions of the virus essential to its replication or life cycle and are by nature strongly conserved may be used. This is particularly important in developing vaccines against highly mutating viruses such as retroviruses (e.g. HIV).

Peptides and other antigens can be combined together and delivered by the immunomodulators to enhance or modulate the immune response.

Further embodiments of the invention relate to the superantigen SMEZ-2 having a defective TcR binding site. Preferably SMEZ-2 has one or more mutation at positions 18, 42, 75 and 182 of the amino acid sequence of SEQ ID NO:1. More preferably, the mutations are chosen from the group consisting of: Y18A; W75L; K182Q; and, D42C. In particularly preferred embodiments relate to SMEZ-2 having the mutations Y18A, W75L, K182Q, and D42C (M2; SEQ ID NO:3), and SMEZ-2 having the mutations W75L, K182Q, and D42C (M1; SEQ ID NO:2).

Persons of general skill in the art to which the invention relates will readily appreciate methods for making a SMEZ-2 superantigen having a defective TcR binding site in accordance with the invention. These methods include isolation from natural sources, recombinant production, chemical synthesis, and techniques described elsewhere herein.

The invention also provides nucleic acids encoding SMEZ-2 mutants of the invention and constructs comprising same. Nucleic acids in accordance with the invention may be DNA, RNA or cDNA for example, double stranded or single stranded, sense or antisense and may include recombinant constructs containing nucleic acids encoding SMEZ-2 mutants of the invention.

Those of general skill in the art to which the invention relates will readily be able to identify nucleic acids which encode SMEZ-2 mutants encompassed by the invention. This may be done on the basis of the amino acid sequences provided herein, the genetic code, and the understood degeneracy therein. Nucleic acids encoding SMEZ-2 mutants encompassed by the invention may also be identified and isolated following screening of genomic or cDNA libraries with nucleic acid probes based on the SMEZ-2 amino acid sequence exemplified herein, or isolated from natural sources using such probes.

The present invention will now be exemplified more particularly with reference to non-limiting examples. The specific examples provide evidence of the improved efficacy of the immunomodulatory constructs of the invention in methods for treatment. In one example, a construct has been developed which includes a SMEZ-2 mutant called M1 coupled to the antigen ovalbumin. Ovalbumin alone is a poor immunogen in mice and does not generate a strong antibody response.

However ovalbumin coupled to a TcR ablated M1 generates a dramatically increased titre (10-fold) to anti-ovalbumin antibodies. Moreover, this antibody was found to be of the IgG1 subclass which indicates that Ig class switching has occurred. This is a sign that the B cells producing the antibody are likely to develop memory cells that ensure a long lasting production of high-titred antibody. Thus M1:ovalbumin constructs illustrate a profoundly enhanced immunogenicity and generate high affinity IgG1 antibodies that are important for a long-lived, protective humoral immune response.

A further construct was prepared using synthetic peptides from the tetanus toxoid (TT) protein which is used to vaccinate humans. These peptides were used to examine a naturally occurring response in a human and to determine whether peptides coupled to defective TcR binding SMEZ-2 were able to stimulate resting memory human T cells more effectively than the peptide alone. The peripheral blood lymphocytes were taken from a person who was vaccinated 10 years prior to this experiment. The results illustrate that a construct comprising TT peptide conjugated to specific SMEZ-2-based molecules was active at concentrations more than 10,000,000 times lower than a TT peptide alone. Higher anti-TT specific responses were seen in the patient with 100 fg/ml of construct of TT versus 10 µg/ml of TT peptide representing a very substantial increase in the immunogenicity of the TT peptide when it is coupled to TcR ablated superantigen. The precursor frequency of anti-TT T cells also appears greater when stimulated by the M1:peptide constructs. This suggests that the construct stimulates both low affinity T cell clones that were not stimulated by the naked TT peptide.

These results indicate the extraordinary increase in immunogenicity of at least constructs based on mutants of SMEZ-2 in humans and illustrate that they may be used to substantially improve human and animal vaccines, treatments and provide biological assays.

EXAMPLES

The inventors have previously disclosed in WO 02/45739 methods for constructing immunomodulatory constructs and a variety of immunomodulatory constructs. WO 02/45739 disclosed methods of cloning superantigens, the ablation of TcR binding sites in superantigens, the construction of various immunomodulatory constructs from various synthetic and natural peptides and/or antigens, and their efficacy in biological systems. The present examples relate to specific SMEZ-2-based immunomodulatory constructs. The SMEZ-2 constructs display better than expected MHC response and general potency.

The aim of these studies was to produce mutants which stimulate T cells at, for example, about 0.0001% of the activity of the wild type SAG.

SMEZ-2 is an allelic variant of SMEZ. Targeted mutagenesis of the TcR binding site allowed the inventors to generate a mutant with >$10^5$-fold decrease in T cell mitogenicity. FIG. 1 illustrates a >$10^5$-fold decrease in T cell mitogenicity results for mutations a three specific residues in the in the SMEZ-2 molecule.

Cloning, Expression and Mutation of SMEZ-2 Gene
a) SMEZ-2 Y18A
b) SMEZ-2 D42A
c) SMEZ-2 W75L
d) SMEZ-2 K182Q
e) SMEZ-2 D42C,W75L, K182Q (M1)
f) SMEZ-2 Y18A, D42C, W75L, K182Q (M2)

All mutants were created by overlap PCR. This is a two-step method in which the required mutation is introduced in both DNA strands separately, followed by annealing and amplification of the two strands.

For the first step, all PCR reactions were carried out in 0.5 ml PCR tubes (SSI, Ca, USA) with 500 ng of pGEX-3c: SMEZ-2 wt DNA (template), 0.2 µM of each primer, 100 µM of each dNTP (GibcoBRL), 2.5 mM $MgCl_2$, and 1U Taq DNA polymerase (Promega). Each PCR was overlayed with mineral oil or the like to prevent evaporation of the reaction mix during cycling. PCR cycling was run under the following conditions using a Perkin Elmer Cetus Thermo Cycler: denaturation at a temperature of 94° C. for 30 seconds, annealing at a temperature of from 53° C. for 45 seconds and extension at a temperature of 72° C. for 30 seconds. 15 cycles were run.

The DNA fragments were run on 1% agarose gels in Tris Acetate buffer, stained with a solution of 40 µg/ml Ethidium bromide and cut out under ultraviolet light. The DNA fragments were extracted from the agarose pieces using the Ultra-Clean™ 15 DNA purification kit (MOBIO laboratories Inc., Solana Beach, Calif., USA) according to instructions of the manufacturer.

For the second step, another PCR was carried out using the same PCR protocol as described above, with the exception of: a) 50 ng of each of the two purified PCR products from the first step were used as templates b) pGEX upper and pGEX lower primers were used, c) annealing was at 48 C, and d) 20 cycles were run.

Primer Combinations Used for First-step PCR:
a) SMEZ-2 Y18A: SMEZ-2 Y18A.fw/pGEX-lower and SMEZ-2 Y18A. rev/pGEX-upper.
b) SMEZ-2 D42A: SMEZ-2 D42A.fw/pGEX-lower and SMEZ-2 D42A.rev/pGEX-upper
c) SMEZ-2 W75L: SMEZ-2 W75L.fw/pGEX-lower and SMEZ-2 W75L.rev/pGEX upper
d) SMEZ-2 R182Q: SMEZ-2 R182Q.fw/pGEX-lower and SMEZ-2 R182Q.rev/pGEX-upper Primer Sequences:
a) SMEZ-2 Y18A.fw: CGATTGTAGCTGAATATTCA-GATATAG (SEQ ID NO:4)
b) SMEZ-2 Y18A.rev: GAATATTCAGCTACAATCGTAC-TATAG (SEQ ID NO:5)
c) SMEZ-2 D42C.fw: GATGTTAGATGTGCTA-GAGATTTC (SEQ ID NO:6 )
d) SMEZ-2 D42C.rev: CTCTAGCACATCTAACAT-CAAGTTTC (SEQ ID NO:7)
e) SMEZ-2 W75L.fw: CCATTTGATTTGAACTATTTATC (SEQ ID NO:8)
20f) SMEZ-2 W75L.rev: GATAAATAGTTCAAAT-CAAATGG (SEQ ID NO:9)
g) SMEZ-2 K182Q.fw: GATATAGAGATCAAGAAAG-TATC (SEQ ID NO:10)
h) SMEZ-2 K182.rev: GATACTTTCTTGATCTCTATATC (SEQ ID NO:11)
i) pGEX-upper: ACCATCCTCCAAAATCGG (SEQ ID NO:12)
j) pGEX-lower: TCAGAGGTTTTCACCGTC (SEQ ID NO:13)

All primers were commercially manufactured by GIBCO BRL.

The quadruple mutant was created by sequential introduction of the 4 mutations. First, pGEX-3c:SMEZ-2 K182Q was used as a template to create SMEZ-2 W75L,K182Q. This double mutant was cloned in pGEX-3c and then used as a template to create SMEZ-2 D42C,W75L, K182Q (M1). Finally, the pGEX-3c:M1 triple mutant served as a template to create the M2 quadruple mutant SMEZ-2 Y18A, D42C, W75L, K182Q.

Expression and Purification of Recombinant SMEZ-2 Mutants

Overlap PCR fragments were digested using restriction enzymes BamHI and EcoRI (LifeTech), and cloned into pGEX-3c expression vector. This vector is a modified version of pGEX-2T (Pharmacia Biotec) that expresses the highly specific protease 3C cleavage site from a picornavirus (Walker et al, 1994[3]) just upstream of the inserted DNA. Recombinant SMEZ-2 mutants were expressed in E. coli DH5 as Gluthathione-S-transferase (GST) fusion proteins. Cultures were grown at 37 degrees C. and induced for 3-4 h after adding 0.2 mM isopropyl-β-D-thiogalactopyranoside (IPTG).

The GST fusion proteins were purified on glutathione (GSH) agarose and the mutant proteins were cleaved off from GST using protease 3C (provided by Keith Hudson, University of Oxford, Oxford, UK) overnight at room temperature. The mutant proteins were further purified by two rounds of cation exchange chromatography using carboxy methyl sepharose (Pharmacia Biotec).

Gel Electrophoresis

All purified recombinant toxins were tested for purity on a 12.5% SDS-polyacrylamide gel electrophoresis.

Amino Acid Sequence Information

Sequence details for wild-type SMEZ-2 and mutants generated by the above method are described below:

Purification of Recombinant Wild-type and Mutant Proteins

SMEZ wild type (wt) and/or mutant proteins were purified by cation exchange chromatography. Briefly, the cleaved fusion protein containing both GST and SMEZ-2 was dialysed overnight in 1L 10 mM $PO_4$ pH6.0 and loaded onto a 10 ml column of CM Sepharose (Pharmacia) pre-equilibriated with the same buffer. Under these conditions only the SMEZ-2 binds and the GST elutes. Purified SMEZ-2 wt and/or mutants were then eluted from the column with 50 mM $PO_4$ pH6.8. Purification by CM Sepharose chromatography was repeated a second time as above. SMEZ-2 wt and/or mutants were sterile filtered and stored in a 50 mM phosphate buffer at 1 mg/ml at 4° C.

T Cell Proliferation Assay of TcR Binding Defective Versions of SMEZ

TcR binding mutants of SMEZ-2 using site directed mutagenesis were prepared as above mentioned. The effect of the SMEZ-2 mutants on T cell proliferation was studied using a standard thymidine incorporation assay. Human peripheral blood lymphocytes from healthy human donors were incubated at $5 \times 10^5$ cells/well in flat bottomed 96-well plates with varying dilutions of purified superantigen mutants and incubated for 3 days at 37° C. After 3 days, 10 uCi of $^3$H thymidine was added and the cells harvested on a cell harvester on day 4. $^3$H thymidine incorporation into DNA was measured by scintillation autography as a measure of lymphocyte proliferation.

Comparative data of mutant vs wild-types on T cell proliferation are presented in Table 2.

TABLE 2

| | SMEZ mutants defective in TcR binding | |
|---|---|---|
| Mutant | P50% (pg/ml) | Reduction |
| SMEZ-2 wild type | 2.0 pg/ml | |
| SMEZ-2 W75L | >10 ng/ml | >100,000 |
| SMEZ-2 D42C | 10 ng/ml | 10,000 |

```
SMEZ2 wild-type
                                                       (SEQ ID NO:1)
LEVDNNSLLR NIYSTIVYEY SDIVIDFKTS HNLVTKKLDV RDARDFFINS EMDEYAANDF

KTGDKIAVFS VPFDWNYLSK GKVTAYTYGG ITPYQKTSIP KNIPVNLWIN GKQISVPYNE

ISTNKTTVTA QEIDLKVRKF LIAQHQLYSS GSSYKSGRLV FHTNDNSDKY SFDLFYVGYR

DKESIFKVYK DNKSFNIDKI GHLDIEIDS*

M1 mutant
                                                       (SEQ ID NO:2)
LEVDNNSLLR NIYSTIVYEY SDIVIDFKTS HCLVTKKLDV RDARDFFINS EMDEYAANDF

KTGDKIAVFS VPFDWNYLSK GKVTAYTYGG ITPYQKTSIP KNIPVNLWIN GKQISVPYNE

ISTNKTTVTA QEIDLKVRKF LIAQHQLYSS GSSYKSGRLV FHTNDNSDKY SFDLLYVGYR

DQESIFKVYK DNKSFNIDKI GHLDIEIDS*

M2 mutant
                                                       (SEQ ID NO:3)
LEVDNNSLLR NIYSTIVAEY SDIVIDFKTS HCLVTKKLDV RDARDFFINS EMDEYAANDF

KTGDKIAVFS VPFDWNYLSK GKVTAYTYGG ITPYQKTSIP KNIPVNLWIN GKQISVPYNE

ISTNKTTVTA QEIDLKVRKF LIAQHQLYSS GSSYKSGRLV FHTNDNSDKY SFDLLYVGYR

DQESIFKVYK DNKSFNIDKI GHLDIEIDS*
```

TABLE 2-continued

SMEZ mutants defective in TcR binding

| Mutant | P50% (pg/ml) | Reduction |
|---|---|---|
| SMEZ-2 W75L.D42C.K182Q (M1) | >10 ng/ml | >100,000 |
| SMEZ-2 Y18A | >10 ng/ml | >100,000 |
| SMEZ-2 W75L.D42C.K182Q.Y18A. (M2) | >10 ng/ml | >100,000 |

Anti-tumour Immunity—In Vivo Tumour Protection.

Many novel cancer immunotherapies attempt to break host tumour tolerance by targeting potential tumour specific antigens (usually lineage specific or differentiation antigens) directly to dendritic cells.

The inventors demonstrate herein that TcR defective SMEZ-2-based constructs usefully target tumour specific antigens to APCs and promote co-stimulatory signals that enhance antigen presentation.

Triple (M1) and quadruple (M2) TcR−/− SMEZ-2 were coupled according to the peptide coupling methodology described in WO 02/45739 to LCMV peptide (having the sequence CKAVYNFATM) and emulsified with an equal volume of incomplete Freund's adjuvant (IFA). Superantigen-LCMV was injected equivalent to 1 μg peptide and compared with 100 μg of peptide emulsified with IFA injected s.c. into the right flank of groups of C57BL6/J mice (n=5). Seven days after immunisation, mice were challenged with $1\times10^6$ LL-LCMV tumour cells injected s.c. into the left flank. The LL-LCMV cells are Lewis lung carcinoma cells (LLTC) transfected with a minigene for the LCMV $_{33-41}$ peptide and can be recognized as targets in vivo in mice of H-$2^b$ background. Mice were monitored every 3-4 days and sacrificed, once 1 mouse in each group had tumours reaching 16 mm in diameter or 200 mm$^2$ in area.

Figure 4A:
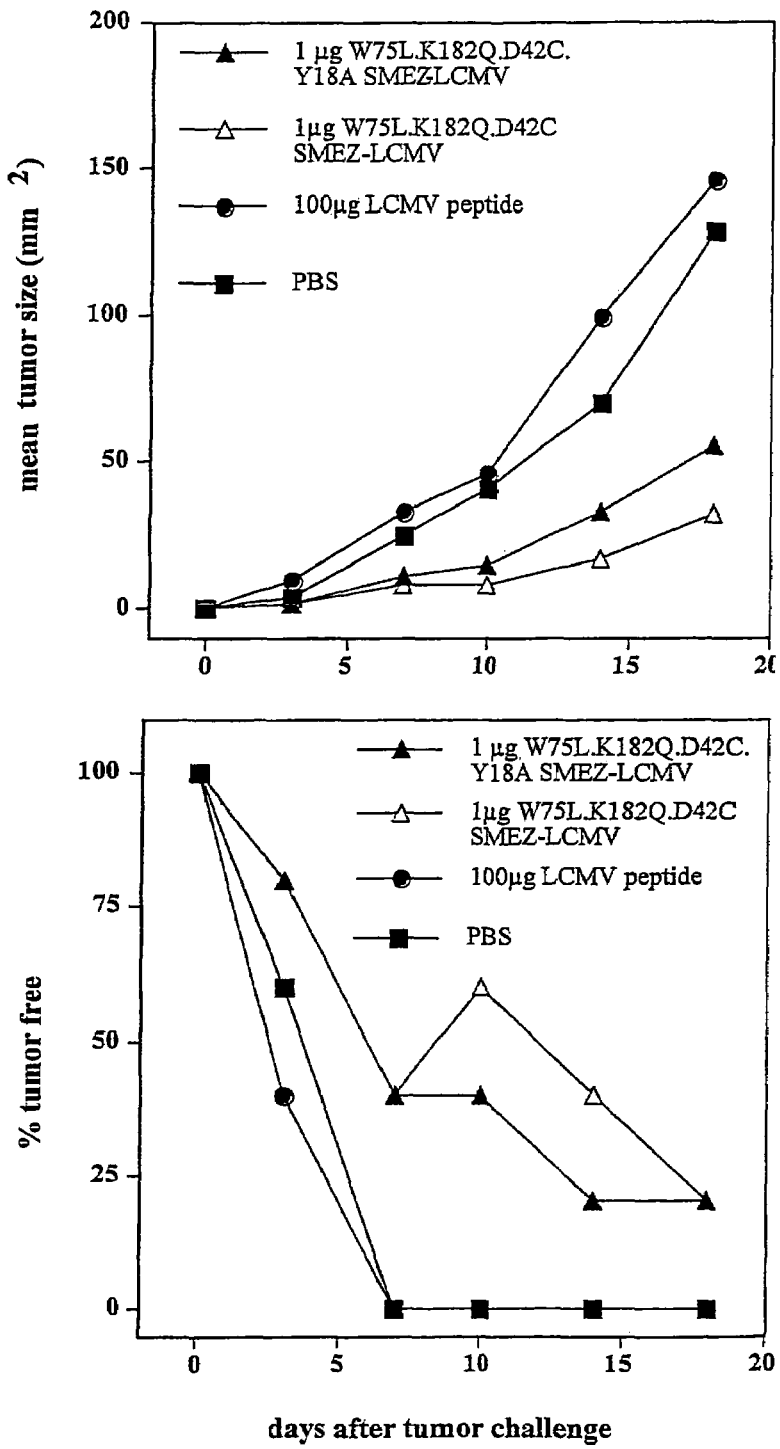
FIG. 4a Inhibition of tumour growth by immunisation with SMEZ-LCMV complexes. Inhibition of tumour growth in C57Bl/6 mice prior immunised with a single dose of M1-LCMV construct compared with 100 µg of LCMV peptide alone and then challenged with $1 \times 10^6$ Lewis Lung carcinoma cells expressing the LCMV peptide.
Figure 4B:
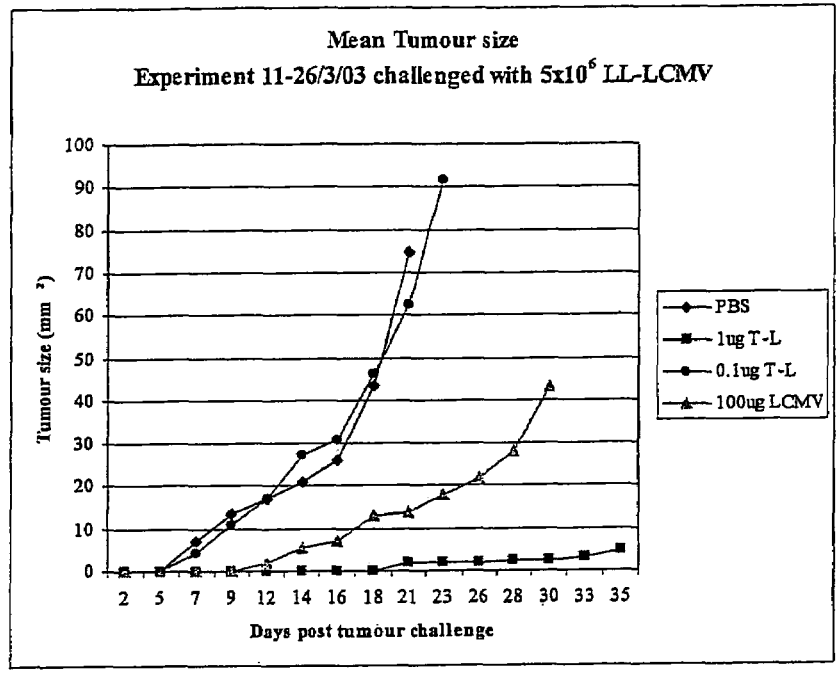
FIG. 4b Inhibition of tumour growth by a single 1 µg dose of M1-LCMV construct followed by a challenge of a $5 \times 10^6$ tumour cells expressing the LCMV peptide. Mice immunised with 1 µg M1-LCMV had significantly slower tumour growth or no tumour growth at all compared to the control of mice immunised with 100 µg of LCMV peptide alone.
Figure 4B:
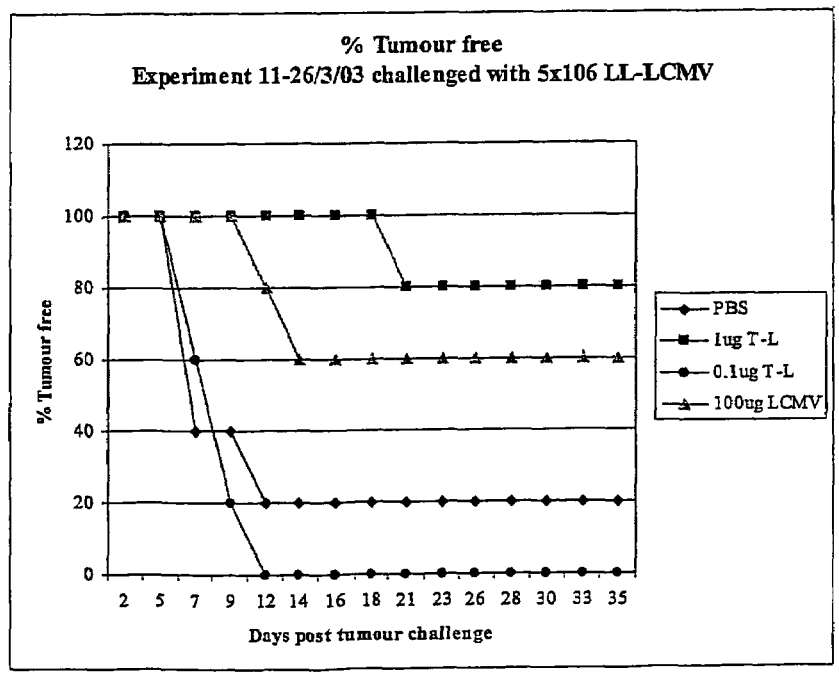

Tumor size is shown as the arithmetric means of the products of bisecting tumor diameters (FIG. 4a show results of this experiment. FIG. 4b shows the results of a similar experiment where mice were challenged with 5 time more tumour cells). The results illustate that a mouse immunised with SAg-LCMV appear to inhibit tumour growth when challenged by LL-LCMV and indicates that an LCMV specific immune response was generated by immunisation with substantially lower LCMV peptide when conjugated to SMEZ-2 mutant than peptide alone.

It is invisaged that the SAG-peptide complexes could be provided in a phamaceutically acceptable form for the treatment of tumours and/or cancers.

Enhanced Antibody Response to Antigens Coupled to SMEZ-2

M1 was coupled to an ovalbumin protein. Ovalbumin is a storage protein which elicits an immune response. Ovalbumin alone is a poor immunogen in mice and does not generate a strong antibody response. This experiment was conducted in order to illustrate that the immunogenicity as measured by the production of specific high affinity antibody to an antigen or protein can be substantially increased when it is delivered as a construct.

M1 was coupled to the ovalbumin protein by the procedure outlined below.

Method Used for Coupling M1 to Ovalbumin
Step 1: Thiolation of Protein by SATP
a. Ovalbumin was dissolved in 50 mM NaPO$_4$, pH 7.5 at a concentration of 5-10 mg/ml
b. SATP was dissolved in DMSO at a concentration of 10 mg/ml (41 μmol/ml)
c. SATP was then added to ovalbumin at a molar ratio of 1:1
d. This was incubated for 2 hours at room temperature.

Step 2: Removal of Free SATP
e. Unbound SATP was removed by passing through 0.5 ml VIVASPIN (VivaScience AG, Hannover) concentrator (5 kDa size exclusion), at 10,000 rpm for 5 min.
f. 0.5 ml of 50 mM NaPO$_4$ at pH 7.5 is added then centrifugation repeated. This is repeated 5 times.
g. Alternatively, SATP-ovalbumin was passed through a 1.5 ml sephadex G35 desalting column.
h. The SATP-ovalbumin was then concentrated to 5 mg/ml using the VIVASPIN column.

Step 3: Coupling Protein-SATP with SMEZ-2 MI
i. Deacetylate protected sulfhydryl group of SATP-ovalbumin immediately after removal of free SATP by adding 10% (v/v) deacetylation solution (50 mM NaPO$_4$, 25 mM EDTA, 0.5 M Hydroxylamine-HCl, pH 7.5)
j. SMEZ-MI is then added to SATP-ovalbumin at a molar ratio of 1:10 (SMEZ-2 MI: protein-SATP)
k. 10 (v/v) coupling buffer (2 M Tris pH 8.5, 20 μM CUSO$_4$) is then added
l. This is then incubated at room temperature for 2 hours The construct was then separated from free reactants by size exclusion chromatography on HPLC using Superose12 (Pharmacia) column.

Four groups of 2 mice (2-week old Balb/c) were immunized subcutaneously with 10 g of:
1. M1
2. Ovalbumin
3. SMEZ M1+Ovalbumin
4. SMEZ M1: Ovalbumin construct The samples of M1, ovalbumin, M1+ovalbumin and M1:Ovalbumin constructs 1 to 4 (above) were emulsified with an equal volume of incomplete Freund's adjuvant (IFA).

At 11 days following the initial immunisation, mice were boosted with a further 10 μg of ovalbumin. The mice were bled at day 0, 11 and 21 following the initial immunisation.

Antibodies to ovalbumin were measure using a standard ELISA method as is well known in the art. ELISA plates were coated with 5 μg/ml ovalbumin.

Results at day 21 following the initial immunisation reveal substantially enhanced anti-ovalbumin responses in mice immunised with the SMEZ M1 :Ova construct compared to mice immunised with either a mix of M1 and Ova or just ovalbumin alone.

The actual titres of anti-Ova antibodies in each of the mice were determined from a standard dilution series of serum (Table 3). The titre of anti-Ovalbumin at day 22 was 1:1280 in the mice immunised with the construct compared with 1:80 in mice immunised with a mix of both Ovalbumin and M1. This represents an enhancement of approximately 16-fold (see FIG. 5).

As mentioned ovalbumin alone is a poor immunogen in mice and does not generate a strong antibody response. However the ovalbumin coupled to M1 displayed dramatically increased titres (16-fold) of anti-Ovalbumin antibody.

Moreover, this antibody was the IgG1 subclass which indicates that Ig class switching has occurred. Thus SMEZ-2: ovalbumin construct illustrates a profoundly enhanced immunogenicity and generate high affinity IgG1 antibodies that are essential to long-lived, protective humoral immune response.

TABLE 3

Anti-Ova titres in immunized mice
(data are averaged over 2 mice per group)

|  | Day 0 | Day 11 | Day 22 |
|---|---|---|---|
| SMEZ | 0 | 1:11 | 0 |
| Ovalbumin | 0 | 0 | 1:160 |
| SMEZ:Ova | 0 | 1:40 | 1:1280 |
| SMEZ + Ova | 0 | 0 | 1:80 |

M1 Presentation of Tetanus Toxoid Peptides to Naturally Occurring Human Memory T Cells A construct was prepared using synthetic peptides, p2 and p30, from the tetanus toxbid (TT) protein. These peptides were used to examine a naturally occurring response in a human and to determine whether peptides coupled to TcR ablated SMEZ-2 were more potent in stimulating existing human anti-TT T cells than the peptide alone. This is an extremely common vaccine in humans and is known to elicit long lasting T and B cell memory responses.

Peptides p2 and p30 are considered "universal" epitopes of the tetanus toxoid (TT) antigen (Valmori D et al, 1992[4])

A p2 TT was coupled to M1 in the same way as described above. Quantitative coupling was observed for both constructs. This was measured by determining the amount of remaining free M1 unconjugated by SDS polyacrylamide gel electrophoresis which migrates at a slightly lower molecular weight. Quantitative, as used above, refers to the fact that all the SMEZ-2 was observed as a higher molecular weight species on SDS PAGE.

Peripheral blood lymphocytes were seeded into 96 well plates at $5\times10^5$/well. Antigen was added at a fixed concentration. T cell proliferation was measured at 3 days by $^3$H thymidine incorporation.

Any wells were assigned as positive if they have a $^3$H thymidine incorporation that was greater than the background ±3 standard deviations.

The patient used was last vaccinated against tetanus 10 years ago.

TABLE 4

| Antigen | Peptide concn. | wells positive/total seeded |
|---|---|---|
| SMEZ-2 wt | 100 pg/ml | 24/24 |
| M1 | 100 pg/ml | 0/24 |
| TT protein | 1 μg/ml | 13/24 |
| TT p2 | 10 μg/ml | 2/12 |
| TT p2 | 1 μg/ml | 1/12 |
| M1:p2 | 0.5 pg/ml | 19/24 |
| TT p30 | 10 μg/ml | 4/12 |
| TT p30 | 1 μg/ml | 0/12 |
| M1:p30 | 0.12 pg/ml | 24/24 |

The results illustrate that a construct of TT was active at concentrations more than 10,000,000 times lower than a TT peptide alone. Higher anti-TT specific responses were seen in the patient with 120 fg/ml of construct of TT versus 100 μg/ml of TT peptide representing a very substantial increase in the immunogenicity of the TT peptide when it is coupled to TcR ablated superantigen.

The precursor frequency of anti-TT T cells appears greater when stimulated by the M1:peptide constructs. This suggests that the construct stimulates both low affinity T cell clones that were not stimulated by the naked TT peptide.

This increased sensitivity was manifest in two ways.

1. The amount of Sag:peptide required was 10,000,000 times less than peptide alone.
2. The anti-p2 and anti-p30 precursor frequency increased above the precursor frequency observed for the uncoupled peptide. Given that $5\times10^5$ PBL were seeded per well and not all cells were positive, then the precursor frequency measured using free peptide must be <1 in $10^5$. The frequency with conjugated peptide >1 in $10^5$ and may be higher.

These results indicate the extraordinary increase in immunogenicity of at least the SMEZ-2:antigen constructs of the invention in humans and illustrate that they may be used to substantially improve human and animal vaccines, treatments and assays.

Coupling of helper T cell peptides to superantigen dramatically increases the antigenicity towards naturally occurring human memory T cells.

In Vitro Cytotoxic Assays: JAM Test

Cytotoxic T lymphocytes (CTL) were generated by culturing lymph node cells from 318 mice for 5 days in 24 well plates ($2.5\times10^6$/ml) in the presence of serially diluted superantigen-peptide complexes (constructed as described in WO 02/45739) or cysLCMV peptide. Cells were fed on day 3 with rhIL-2 and RPMI. At day 5, cells were washed twice and assayed for CTL activity by the JAM test (Matzinger, 1991[5]). Briefly, EL4 cells were incubated with 5 μCi/ml [$^3$H]thymidine overnight, the next day LCMV peptide was added at 1 nM for 3 hrs. Cells were washed twice and used as target cells for LCMV-specific CTL generated with superantigen-LCMV complexes as mentioned in FIG. 6: CTL and EL4 cells were incubated together at various effector:target (E:T) ratios for 3 hrs. The percentage of specific lysis was calculated using the following equation:

$$\%\ \text{Specific Lysis}\ \frac{S-E}{S}\times 100$$

S=retained DNA in the absence of killers (CPM), and E=retained DNA in presence of killers (CPM). Results are shown in FIG. 6.

Synthetic LCMV peptide modified at position 8 (M8C) was coupled to SPEC-Y15A.C27S.N79C.R181Q using the method as described above. Superantigen:LCMV was used to determine the in vitro response in lymph node cells from 318 mice. The last residue in the peptide (position number 8) was changed from a methionine to a cysteine to allow it to be coupled by disulphide bridge, to the superantigen.

Advantages of the invention herein described will be readily appreciated by skilled persons particularly having regard to the Examples above. However, some of the advantages and features of the exemplary TcR defective immunomodulatory constructs of the invention are the following:

a. The superantigen is totally defective in binding to all TcRs and thus will be non-toxic in vivo.

b. Coupling of peptides is simple, efficient and reversible and broadly applicable.

c. The superantigen:peptide construct is soluble.

d. superantigen binding to MHC class II enhances APC activation of immunogenic and non-immunogenic moieties.

e. The SMEZ-2-based constructs of the invention have high potency and better than expected MHC response.

Where in the foregoing description reference has been made to integers with specific components or integers of the invention having known equivalents, then such equivalences are herein incorporated as if individually set forth.

Although the invention has been described by way of example and with reference to possible embodiments thereof, it will be understood that modifications or improvements may be made thereto without departing from the scope or spirit of the invention.

Throughout this specification, unless the context requires otherwise, the words "comprise", "comprising" and the like, are to be construed in an inclusive sense as opposed to an exclusive sense, that is to say, in the sense of "including, but not limited to".

The reference to any prior art in this specification is not, and should not be taken as, an acknowledgment or any form of suggestion that that prior art forms part of the common general knowledge in any country of the world.

REFERENCES

1. Terman (WO98/26747)
2. Marrack, P., Blackman, M., Kushnir, E. & Kappler, J. The toxicity of staphylococcal enterotoxin B in mice is mediated by T cells. *J Exp Med* 171, 455-64 (1990).
3. Walker et al 1994.
4. Valmori D., Pessi A., Bianchi E, Corradin G 1992 Use of human universally antigenic tetanus toxin T cell epitopes as carriers for human vaccination *J. Immunol.* 149 717-712
5. Matzinger, P., 1991, J immunol methods, 145:185-192

The invention claimed is:

1. A construct which comprises an antigen-presenting-cell (APC) targeting molecule coupled to an antigen, wherein said APC targeting molecule contains a mutant of superantigen SMEZ-2 having the amino acid sequence of SEQ ID NO:1, wherein the mutant has a mutation at one or more positions of 18, 42, 75, and 182 in SEQ ID NO:1 and wherein the construct can bind to Class II MHC molecules.

2. The construct of claim 1, wherein the mutant of superantigen SMEZ-2 has a mutation at position 18 in SEQ ID NO:1, or C at position 42 (D42C) in SEQ ID NO:1.

3. The construct of claim 2, wherein the mutant of superantigen SMEZ-2 has C at position 42 (D42C) in SEQ ID NO:1.

4. The construct of claim 2, wherein the mutant of superantigen SMEZ-2 has A at position 18 (Y18A) in SEQ ID NO:1.

5. The construct of claim 1, wherein the mutant of superantigen SMEZ-2 has A at position 18 (Y18A) in SEQ ID NO:1, C at position 42 (D42C) in SEQ ID NO:1, L at position 75 (W75L) in SEQ ID NO:1, and Q at position 182 (K182Q) in SEQ ID NO:1.

6. The construct of claim 1, wherein the mutant of superantigen SMEZ-2 has C at position 42 (D42C) in SEQ ID NO:1, L at position 75 (W75L) in SEQ ID NO:1, and Q at position 182 (K182Q) in SEQ ID NO:1.

7. The construct of claim 1, wherein the APC targeting molecule is coupled to ovalbumin.

8. The construct of claim 1, wherein the APC targeting molecule is coupled to tetanus toxoid (TT) or a peptide thereof.

9. The construct of claim 1, wherein the APC targeting molecule is coupled to LCMV peptide.

10. The construct of claim 1, wherein the coupling between the antigen-presenting-cell (APC) targeting molecule and the antigen is reversible.

11. The construct of claim 1, wherein the antigen is a protein or a peptide.

12. A pharmaceutical composition comprising the construct of claim 1 and one or more pharmaceutically acceptable carriers, adjuvants, excipients and/or solvents.

13. A vaccine comprising the construct of claim 1.

14. A method of preparing the construct of claim 1 comprising the steps of:
   a. introducing a mutation at one or more positions of 18, 42, 75, and 182 in SEQ ID NO:1 to produce a mutant of superantigen SMEZ-2, and
   b. coupling the mutant of SMEZ-2 to an antigen.

15. A construct prepared by:
   a. introducing a mutation at one or more positions of 18, 42, 75, and 182 in SEQ ID NO:1 to produce a mutant of superantigen SMEZ-2, and
   b. coupling the mutant of SMEZ-2 with an antigen.

16. A superantigen, which has the amino acid sequence of SEQ ID NO:1 but for a mutation at one or more positions of 18, 42, 75 and 182 in SEQ ID NO:1.

17. A superantigen as claimed in claim 16, wherein the superantigen has:
   Y18A;
   W75L;
   K182Q; or
   D42C.

18. A superantigen SMEZ-2 having the amino acid sequence of SEQ ID NO:2.

19. A superantigen SMEZ-2 having the amino acid sequence of SEQ ID NO:3.

* * * * *